United States Patent
Mayer

(10) Patent No.: US 9,128,045 B2
(45) Date of Patent: Sep. 8, 2015

(54) ELECTROCHEMICAL SENSOR WITH ZERO CALIBRATION FEATURE AND METHOD OF CALIBRATING

(75) Inventor: Daniel W. Mayer, Wyoming, MN (US)

(73) Assignee: MOCON, Inc., Minneapolis, MN (US)

( * ) Notice: Subject to any disclaimer, the term of this patent is extended or adjusted under 35 U.S.C. 154(b) by 644 days.

(21) Appl. No.: 11/734,444

(22) Filed: Apr. 12, 2007

(65) Prior Publication Data

US 2008/0251379 A1    Oct. 16, 2008

(51) Int. Cl.
*G01N 27/416* (2006.01)
*G01N 27/404* (2006.01)

(52) U.S. Cl.
CPC .......... *G01N 27/4163* (2013.01); *G01N 27/404* (2013.01)

(58) Field of Classification Search
CPC .................... G01N 27/404; G01N 27/4163
USPC ............. 204/400–435; 205/785.5, 775–794.5
See application file for complete search history.

(56) References Cited

U.S. PATENT DOCUMENTS

| | | | |
|---|---|---|---|
| 3,767,552 A | 10/1973 | Lauer | |
| 3,824,168 A | 7/1974 | Oswin et al. | |
| 3,838,021 A | 9/1974 | Arbiter | |
| 3,909,386 A | 9/1975 | Oswin et al. | |
| 3,940,251 A * | 2/1976 | Jones et al. | 422/84 |
| 3,992,267 A | 11/1976 | Oswin et al. | |
| 4,116,612 A | 9/1978 | Melgaard | |
| 4,132,616 A | 1/1979 | Tantram et al. | |
| 4,151,738 A | 5/1979 | Hyer et al. | |
| 4,321,113 A | 3/1982 | Grambow et al. | |
| 4,322,964 A | 4/1982 | Melgaard et al. | |
| 4,324,632 A | 4/1982 | Tantram et al. | |
| 4,384,925 A | 5/1983 | Stetter et al. | |
| 4,430,164 A * | 2/1984 | Daroczy et al. | 205/781.5 |
| 4,489,590 A | 12/1984 | Hadden | |
| 4,718,991 A * | 1/1988 | Yamazoe et al. | 205/785.5 |
| 4,742,708 A | 5/1988 | Porter | |
| 4,772,375 A * | 9/1988 | Wullschleger et al. | 205/701 |
| 4,829,809 A | 5/1989 | Tantram et al. | |
| 4,833,909 A | 5/1989 | Matthiessen | |
| 5,202,637 A | 4/1993 | Jones | |
| 5,211,154 A * | 5/1993 | Brandt | 123/693 |
| 5,239,492 A | 8/1993 | Hartwig et al. | |
| 5,565,085 A * | 10/1996 | Ikeda et al. | 205/777.5 |
| 5,611,909 A | 3/1997 | Studer | |
| 5,906,718 A * | 5/1999 | Hance et al. | 204/412 |
| 5,976,085 A | 11/1999 | Kimball et al. | |
| 6,066,249 A | 5/2000 | Manzoni et al. | |
| 6,370,940 B2 | 4/2002 | Warburton | |
| 6,926,814 B2 | 8/2005 | Koenemann et al. | |
| 7,022,219 B2 | 4/2006 | Mansouri et al. | |

FOREIGN PATENT DOCUMENTS

DE    10244084 A1    4/2004
GB    1203049    8/1970

(Continued)

*Primary Examiner* — Susan D Leong
(74) *Attorney, Agent, or Firm* — Sherrill Law Offices, PLLC

(57) ABSTRACT

An easily calibrated analytical instrument for sensing a target analyte. The instrument includes an electrochemical sensor and a switch. The electrochemical sensor includes a sensing electrode and a counter electrode. The switch is a normally open switch effective for creating a short circuit between the sensing and counter electrodes when closed. A zero calibration reading can be taken when the switch is closed.

12 Claims, 1 Drawing Sheet

(56) References Cited

FOREIGN PATENT DOCUMENTS

| | | |
|---|---|---|
| GB | 1340084 | 12/1973 |
| GB | 1433071 | 4/1976 |
| JP | 57-192855 | 11/1982 |
| JP | 61-294352 | 12/1986 |
| JP | 05-203616 | 8/1993 |

* cited by examiner

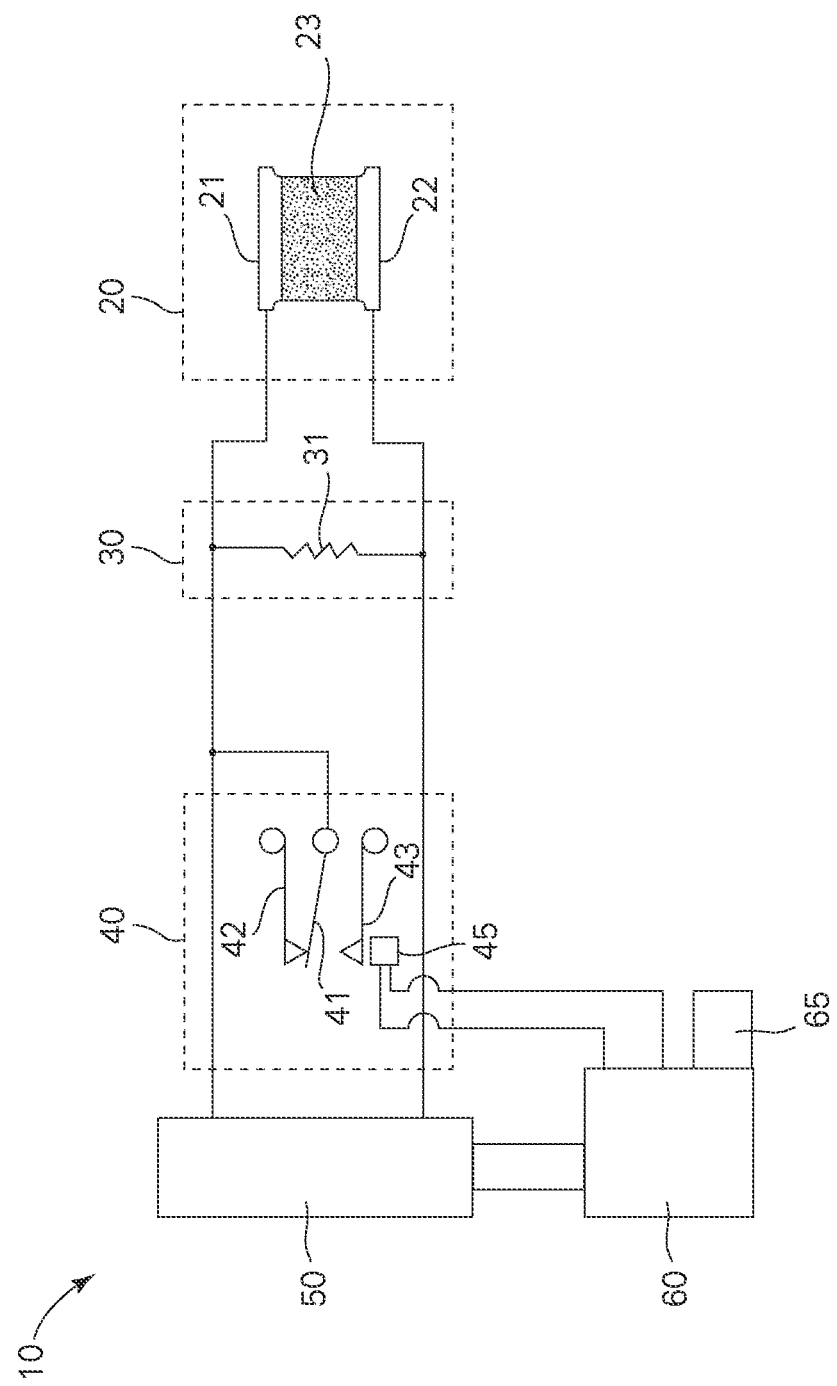

ELECTROCHEMICAL SENSOR WITH ZERO CALIBRATION FEATURE AND METHOD OF CALIBRATING

BACKGROUND

Gas detection and measurement by means of sensors is well known in the art. There are many types of sensors available designed for various applications. One of the most common types of sensors is the electrochemical gas sensor. Such sensors are widely available and described in numerous United States patents, including U.S. Pat. Nos. 3,767,552, 3,824,168, 3,909,386, 3,992,267, 4,132,616 and 4,324,632. Electrochemical sensors are widely used for measuring oxygen concentrations and the concentration of toxic gas detection for work-place safety, emission monitoring and control of pollutants.

Most electrochemical sensors are designed such that a gas of interest is brought into reactive contact with the electrodes such that any target analyte in the gas is oxidized or reduced at a sensing electrode within the sensor. The gas typically passes through one or more diffusion barriers, such as a porous membrane, capillary sintered disk, etc. to reach the electrode. The majority of sensors are operated such that the response current is limited by the rate at which the gas can diffuse into the sensor. A diffusion limited sensor has the advantageous properties of a linear response to the gas concentration, stable output with small changes in operating potential due to environmental or instrumental changes (e.g. variations in power supply voltage), and either a small or at least well defined variation in output with temperature and pressure.

In a typical design, a sensor will contain two or more electrodes within the sensor in contact with an electrolyte. One electrode is designated the sensing electrode. The gas of interest enters the sensor and moves by diffusion through the membrane and any other diffusion barriers in the gas path to the electrode. The gas is consumed at the sensing electrode in either an oxidation or a reduction process, and the resulting electrical charge passes from the electrode, through the external circuit to the counter electrode. The magnitude of this electric current generates an output signal. At the counter electrode, which must also be in contact with the electrolyte, an equal and opposite electrochemical reaction occurs.

The magnitude of the output signal is determined by the concentration of target analyte in the gas, and by the diffusivity of the gas path through which the gas must pass to reach the sensing electrode. The diffusivity is defined here as a measure of how much gas at unit concentration will diffuse into the sensor per second. If the diffusivity of the sensor is known, then the gas concentration can be calculated by measuring the output current from the sensor.

In the operation of electrochemical sensors, it is customary to periodically calibrate the zero and span performance of the sensor in order to re-confirm or re-establish the measurement accuracy. Calibration of the sensor elements is important in achieving accurate measurement with the sensor because sensors and associated electronics tend to suffer from zero drift over time in either a positive or negative direction. In accordance with conventional practice, the zero drift of the sensor element over time is compensated for or adjusted by periodic zero calibrations utilizing a known zero calibration gas composition which contains none of the target gas. A similar problem exists with respect to the sensor and associated electronics span signal which gradually will change over a period of time due to aging of the sensor elements. This may similarly be corrected for or adjusted by periodic span calibrations of the sensor circuitry utilizing a calibration gas which contains a known quantity of test gas.

Calibration of the instrument can be a substantial operational problem as it requires the purchase, storage and use of two different calibration gasses (one with zero target analyte for obtaining a zero calibration reading and the other with a known concentration of target analyte for obtaining a span calibration reading) and the instrument is normally taken off-line for calibration. In many situations, such as in the case of industrial controls, the removal of the sensor from the control process may result in the loss of production time and considerable expense while the process is shut down until the control instrumentation can be calibrated and returned. In the alternative, to avoid shut-down of the process, substitute instruments can be used to replace instruments undergoing calibration. While generally effective for avoiding shut-down, this method requires a larger inventory of instruments.

Methods and apparatus to permit automatic in-line calibrations have been developed, such as those described in U.S. Pat. Nos. 4,116,612, 4,151,738, 4,322,964, 4,384,925, 4,489, 590 and 5,239,492. While generally effective, such devices substantially add to the cost of the instrument. In addition, such instruments still rely on the presence of test gases of known concentration (i.e., a gas containing no target analyte and a gas containing a known concentration of target analyte). For oxygen sensors, ambient air is often used as one of the test gases as the concentration of oxygen in well ventilated areas is a constant 20.9 volume percent. However, a source of oxygen free gas is still necessary to fully calibrate an oxygen sensor.

U.S. Pat. No. 4,829,809 describes a calibration method which does not require a known test gas concentration. The method passes a test gas of unknown concentration over the sensor through a calibration flow system of known volume. After flushing the system, the flow of test gas is stopped and the calibration system is sealed. The output current decays to zero as the sensor consumes target analyte in the gas. Using Faraday's Law, the sensitivity of the initial gas concentration can be found. While generally effective, the process is slow as substantial time is required for the current to decay exponentially to zero, and the process and prone to errors. A similar system is described in U.S. Pat. No. 4,833,909, but is subject to the same problems.

Other approaches have focused on the electrical properties of the sensor. For example, U.S. Pat. Nos. 5,202,637 and 5,611,909 apply a small potential to the normally constant potential between the sensing electrode and the counter electrode and monitor the electrical current response of the sensor. While providing a simple in-situ test that an instrument or controller can automatically perform on the sensor, this method will only detect those modes of sensor failure which affect the electrical properties of the working electrode, such as loss of volume due to dry-out from an aqueous based electrolyte. The test is unable to detect sensor faults resulting from other problems.

Accordingly, a need exists for an inexpensive system and method for quickly, simply, and reliably calibrating an electrochemical sensor.

SUMMARY OF THE INVENTION

A first aspect of the invention is an analytical instrument for sensing a target analyte. The instrument includes an electrochemical sensor and a switch. The electrochemical sensor includes a sensing electrode and a counter electrode. The switch is a normally open switch effective for creating a short circuit between the sensing and counter electrodes when closed. A zero calibration reading can be taken when the switch is closed.

A specific embodiment of the first aspect of the invention includes (i) an electrochemical sensor, (ii) a signaling module, (iii) a switch, and (iv) a microprocessor. The electrochemical sensor includes a sensing electrode and a counter electrode, both in contact with an electrolyte and a test volume, for generating an electrical current proportional to the concentration of target analyte present in the test volume. The signaling module is in electrical communication with the electrochemical sensor for receiving electrical current generated by the electrodes and producing an electrical output signal proportional to the electrical current. The switch is a normally open switch for providing a short circuit between the sensing and counter electrodes when closed, whereby electrical current generated by the electrodes bypasses the signaling module when the switch is closed. The microprocessor contains a zero calibration value in memory and is in electrical communication with the signaling module and the switch. When the switch is open the microprocessor receives the electrical output signal and any background signal and either (A) zero calibrates the electrical output signal employing the zero calibration value in memory in an effort to cancel the background signal, and correlates the zero calibrated electrical output signal to a numerical value indicating the concentration of analyte in the test volume, or (B) correlates the electrical output signal to a numerical value indicating the concentration of analyte in the test volume, and zero calibrates the numerical value of concentration employing the zero calibration value in memory. When the switch is closed the microprocessor receives any background signal and either (A) replaces the zero calibration value in memory with the value of the received background signal, or (B) correlates the received background signal to a numerical value indicating a concentration of analyte and replaces the zero calibration value in memory with the numerical value of concentration.

A second aspect of the invention is a method of zero calibrating an electrochemical sensor. The method includes the steps of (i) obtaining an electrochemical sensor having a sensing electrode and a counter electrode, (ii) short circuiting the electrodes, and (iii) taking a zero calibration reading with the electrodes short circuited.

A specific embodiment of the second aspect of the invention includes the steps of (i) obtaining an electrochemical sensor having (A) a sensing electrode and a counter electrode, both in contact with an electrolyte and a test volume, for generating an electrical current proportional to the concentration of target analyte present in the test volume, (B) a signaling module in electrical communication with the electrodes for receiving electrical current generated by the electrodes and producing an electrical output signal proportional to the electrical current, and (C) a microprocessor for receiving and processing the electrical output signal, (ii) short circuiting the electrodes, and (iii) recording any background signal received by the microprocessor with the electrodes short circuited as the zero calibration value.

BRIEF DESCRIPTION OF THE DRAWINGS

FIG. 1 is an electrical schematic of one embodiment of the invention.

DETAILED DESCRIPTION OF A PREFERRED EMBODIMENT

Nomenclature
10 Instrument
20 Electrochemical Sensor
21 Sensing Electrode
22 Counter Electrode
23 Electrolyte
30 Signaling Module
31 Load Resistor
40 Switch
41 Common Lead
42 Normally Closed Lead
43 Normally Open Lead
45 Switching Relay Coil
50 Amplifier
60 Microprocessor or Microcontroller
65 Memory
Description The instrument 10 of the present invention is an electrochemical sensor 20 capable of providing a zero calibration reading even while the sensors 21 and 22 are exposed to analyte (not shown).

Referring to FIG. 1, the instrument 10 includes an electrochemical sensor 20, a signaling module 30, a switch 40, an amplifier 50, and a microprocessor 60 with memory 65.

The electrochemical sensor 20 includes a sensing electrode 21, a counter electrode 22, and an electrolyte 23 between the sensors 21 and 22. The electrochemical sensor 20 may be selected from any of the widely available electrochemical sensors 20 used to sense an analyte of interest. Common analytes of interest include specifically, but not exclusively, carbon monoxide, oxygen, ozone, water vapor, and volatile organ compounds such as propane, benzene, toluene, methanol, etc.

The electrochemical sensor 20 is effective for consuming target analyte at the sensing electrode 21, thereby generating an electrical charge which passes from the sensing electrode 21 through external circuitry to the counter electrode 22. The magnitude of the electrical charge generated at the sensing electrode 21 is proportional to the amount of target analyte consumed.

The signaling module 30 converts the current generated by the electrochemical sensor 20 to an electrical output signal (typically voltage), with the magnitude of the electrical output signal proportional to the magnitude of the current. A preferred signaling module 30 is a load resistor 31.

The switch 40 is configured and arranged to permit selective short circuiting of the electrical path between the electrodes 21 and 22. The switch 40 shown in FIG. 1 includes a common lead 41, a normally closed lead 42, a normally open lead 43 and a relay coil 45. The common lead 41 is biased to contact the normally closed lead 42. When the common lead 41 contacts the normally closed lead 42 the switch 40 is open and any electrical charge generated at the sensing electrode 21 will flow to the counter electrode 22 through the signaling module 30 and generate an electrical output signal proportional to the electrical charge. When the relay coil 45 is powered, the common lead 41 is "pulled" against the bias into contact with the normally open lead 43. When the common lead 41 contacts the normally open lead 43, the switch 40 short circuits the electrodes 21 and 22, thereby causing any electrical charge generated at the sensing electrode 21 to preferentially flow to the counter electrode 22 through the switch 40 rather than through the signaling module 30 (i.e., the electric charge will flow through the path of least resistance) thereby causing the signaling module 30 to generate an electrical output signal of zero (i.e., signaling that no analyte is detected by the electrochemical sensor 20). Hence, by short circuiting the electrodes 21 and 22, a zero calibration reading can be taken.

The switch 40 may be selected from any of the widely available switches 40, including manually operated and electromagnetically actuated switches 40, with a general preference for electromagnetically actuated switches 40 controlled by the microprocessor 50.

An amplifier 50 is provided to amplify the electrical output signal (typically voltage) generated by the signaling module 30.

The amplified electrical output signal is communicated to the microprocessor or microcontroller 60. During normal operation of the instrument 10 the switch 40 is open. When the switch 40 is open, the microprocessor 60 receives the amplified electrical output signal and any background signal created by the instrument 10, zero calibrates the combination of the amplified electrical output signal and any background signal employing a zero calibration value in memory 65 in an effort to cancel the background signal, and then correlates the zero calibrated electrical output signal to a numerical value indicating the concentration of detected analyte. Alternatively, the microprocessor 60 correlates the combination of the amplified electrical output signal and any background signal to a numerical value indicating the concentration of detected analyte, and then zero calibrates the numerical value of concentration employing a zero calibration value in memory 65 in an effort to cancel the background signal.

In order to calibrate the instrument 10 the switch 40 is closed. When the switch 40 is closed, the microprocessor 60 receives only the background signal and either (A) replaces the zero calibration value in memory 65 with the value of the received background signal, or (B) correlates the received background signal to a numerical value indicating a concentration of analyte and replaces the zero calibration value in memory with the numerical value of concentration.

In some instances, the switch 40 may itself contribute a background signal when the switch 40 is closed and any electrical charge generated at the electrodes 21 and 22 passes through the switch 40. Since this aspect of the background signal is not generated when the switch 40 is open, the switch-contributed portion of background signal should be removed from the zero calibration value. This can be done prior to shipment of the instrument 10 to an end user by (i) obtaining a primary background signal value with the switch 40 closed and the electrodes 21 and 22 exposed to a gas free from target analyte, (ii) obtaining a secondary background signal value with the switch 40 closed and the electrodes 21 and 22 exposed to a gas containing target analyte, (iii) calculating the difference between the secondary background signal value and the primary background signal value to obtain a value for the switch-contributed portion of the background signal, and (iii) programming the microprocessor 40 to subtract the switch-contributed portion of the background signal from any background signal obtained when the switch 40 is closed.

I claim:

1. An analytical instrument, comprising:
   (a) an electrochemical sensor for sensing a target analyte in a test volume, the electrochemical sensor comprising a single sensing electrode and a single counter electrode, both in contact with a common electrolyte and a common test volume, for generating an electrical current proportional to the concentration of target analyte present in the test volume,
   (b) a signaling module in electrical communication with the electrochemical sensor for receiving electrical current generated by the electrodes and producing an electrical output signal proportional to the electrical current,
   (c) a normally open switch for providing an electrical short circuit between the single sensing and single counter electrodes when closed, whereby electrical current generated by the electrodes bypasses the signaling module when the switch is closed, and
   (d) a microprocessor containing a span calibration value and a zero calibration value in memory, the microprocessor in electrical communication with the signaling module and the switch wherein:
      (1) when the switch is open the microprocessor receives an electrical analysis signal comprised of the electrical output signal and any background signal, and either:
         (A) calibrates the electrical analysis signal employing a calibration value derived from the span calibration value and the zero calibration value in memory, and correlates the calibrated electrical analysis signal to a numerical value indicating the concentration of analyte in the test volume, or
         (B) correlates the electrical analysis signal to a numerical value indicating the concentration of analyte in the test volume, and calibrates the numerical value of concentration employing a calibration value derived from the span calibration value and the zero calibration value in memory, and
      (2) when the switch is closed no electrical signal from any electrode reaches the signaling module whereby the microprocessor receives only background signal and either (A) replaces the zero calibration value in memory with the value of the received background signal, or (B) correlates the received background signal to a numerical value indicating a concentration of analyte and replaces the zero calibration value in memory with the numerical value of concentration.

2. The analytical instrument of claim 1 wherein the target analyte is oxygen.

3. The analytical instrument of claim 1 wherein the signaling module includes a load resistor effective for converting the electrical current generated by the electrodes to a voltage.

4. A method of calibrating an electrochemical target analyte sensor, comprising the steps of:
   (a) obtaining an analytical instrument in accordance with claim 1,
   (b) exposing the electrodes to a gas having a known non-zero span concentration of target analyte,
   (c) taking a span calibration reading with the electrodes exposed to the span concentration of target analyte,
   (d) recording the span calibration reading in computer memory,
   (e) electrically short circuiting the electrodes whereby no electrical signal from any electrode reaches the signaling module,
   (f) taking a zero calibration reading with the electrodes short circuited, and
   (g) recording the zero calibration reading in computer memory.

5. The method of claim 4 wherein the electrochemical sensor is an oxygen sensor.

6. The method of claim 4 wherein the electrodes are short circuited by closing the switch.

7. A method of calibrating an electrochemical sensor, comprising the steps of:
   (a) obtaining an electrochemical sensor having (i) a single sensing electrode and a single counter electrode, both in contact with a common electrolyte and a common test volume, for generating an electrical current proportional to the concentration of target analyte present in the test volume, (ii) a signaling module in electrical communication with the electrodes for receiving electrical current generated by the electrodes and producing an electrical output signal proportional to the electrical current, and (iii) a microprocessor containing a span calibration value and a zero calibration value in memory, for receiving and processing the electrical output signal, (b) exposing the electrodes to a gas having a known non-zero span concentration of target analyte, (c) taking a span calibration reading with the electrodes exposed to the span concentration of target analyte, (d) replacing the span calibration value in memory with the value of the span calibration reading, (e) electrically short circuiting the electrodes whereby no electrical signal from any electrode reaches the signaling module, (f) taking a zero calibration reading comprised of any background signal received by the microprocessor with the electrodes short circuited whereby no electrical signal from any electrode reaches the microprocessor, and, (g) replacing the zero calibration value in memory with the value of the zero calibration reading.

8. The method of claim 7 wherein the background signal has a value and this value is recorded as the zero calibration value.

9. The method of claim 7 wherein the background signal is correlated to a numerical value indicating a concentration of analyte and the correlated numerical value of concentration is recorded as the zero calibration value.

10. The method of claim 7 wherein the electrochemical sensor is an oxygen sensor.

11. The method of claim 7 wherein the signaling module includes a load resistor effective for converting the electrical current generated by the electrodes to a voltage.

12. The method of claim 7 wherein the electrodes are short circuited by activation of a switch.

\* \* \* \* \*